United States Patent [19]

Pilkington et al.

[11] Patent Number: 5,185,339
[45] Date of Patent: Feb. 9, 1993

[54] FUNGICIDAL COMPOUNDS

[75] Inventors: Brian L. Pilkington; Paul A. Worthington, Maidenhead, both of England

[73] Assignee: Imperial Chemical Industries PLC, London, England

[21] Appl. No.: 701,386

[22] Filed: May 16, 1991

[30] Foreign Application Priority Data

May 30, 1990 [GB] United Kingdom ............... 9012017

[51] Int. Cl.$^5$ ............... A61K 31/505; C07D 239/20; C07D 239/72
[52] U.S. Cl. ............... 514/256; 514/258; 514/269; 544/253; 544/298; 544/319; 544/333
[58] Field of Search ............... 544/253, 319, 333, 298, 544/219; 514/256, 258, 269

[56] References Cited

U.S. PATENT DOCUMENTS 4,752,608 6/1988 Katoch et al. ............... 544/333

FOREIGN PATENT DOCUMENTS 3937285 5/1991 Fed. Rep. of Germany .
91/07399 5/1991 World Int. Prop. O. .

OTHER PUBLICATIONS

Giencke et al., Chemical Abstract, 115(3) #29367d, 1991.

*Primary Examiner*—Mukund J. Shah
*Assistant Examiner*—Y. N. Gupta
*Attorney, Agent, or Firm*—Lynn Marcus-Wyner

[57] ABSTRACT

Fungicidal compounds having the formula (I):

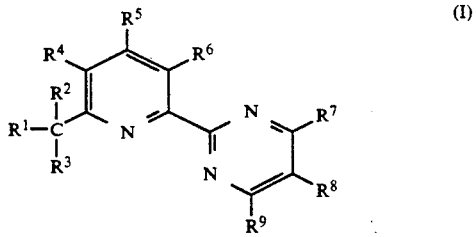

wherein $R^1$ is an optionally substituted phenyl group; $R^2$ and $R^3$, which are the same or different, are hydrogen or $C_{1-4}$ alkyl; $R^4$, $R^5$ and $R^6$, which are the same or different, are hydrogen, $C_{1-4}$ haloalkyl, $C_{1-4}$ alkyl or $C_{1-4}$ alkoxy; $R^7$, $R^8$ and $R^9$, which are same or different, are hydrogen, $C_{1-4}$ alkyl, $C_{1-4}$ haloalkyl, $C_{1-4}$ alkoxy or halogen, or $R^7$ and $R^8$ together form a polymethylene group of the formula —$(CH_2)_m$— in which m is 3 or 4; and, acid addition salts or metal complexes thereof; are useful as fungicides. The invention also relates to processes for preparing them, to fungicidal compositions containing them, and to methods of using them to combat fungi, especially fungal infections in plants.

7 Claims, No Drawings

FUNGICIDAL COMPOUNDS

The present invention relates to pyridylpyrimidine derivatives that are useful as fungicides, to processes for preparing them, to fungicidal compositions containing them, and to methods of using them to combat fungi, especially fungal infections in plants.

According to the present invention there is provided a compound having the general formula (I), wherein $R^1$ is an optionally substituted phenyl group; $R^2$ and $R^3$, which are the same or different, are hydrogen or $C_{1-4}$ alkyl; $R^4$, $R^5$ and $R^6$, which are the same or different, are hydrogen, $C_{1-4}$ haloalkyl, $C_{1-4}$ alkyl or $C_{1-4}$ alkoxy; $R^7$, $R^8$ and $R^9$, which are same or different, are hydrogen, $C_{1-4}$ alkyl, $C_{1-4}$ haloalkyl, $C_{1-4}$ alkoxy or halogen, or $R^7$ and $R^8$ together form a polymethylene group of the formula —$(CH_2)_m$— in which m is 3 or 4; and acid addition salts or metal complexes thereof.

Alkyl groups and the alkyl moiety of the alkoxy group contain from 1 to 4 carbon atoms and are in the form of straight or branched chains, i.e. methyl, ethyl, n-propyl, iso-propyl, n-butyl, iso-butyl, sec-butyl or tert-butyl (t-$C_4H_9$).

Alkenyl groups contain from 2–4 carbon atoms and are alk-1-enyl, alk-2-enyl or alk-3-enyl, for example, vinyl, 2-prop-1-enyl, 1-prop-1-enyl, allyl, 2-but-2-enyl, 1-(2-methylprop-1-enyl), 1-but-1-enyl, 1-(1-methylprop-2-enyl), 1-(2-methylprop-2-enyl), 1-but-2-enyl, or 1-but-3-enyl.

Alkynyl groups contain from 2 to 4 carbon atoms and are, for example, ethynyl, prop-1-ynyl, propargyl or 2-but-3-ynyl.

Halogen includes fluorine, chlorine, bromine and iodine atoms.

Haloalkyl groups contain from 1 to 4 carbon atoms and at least one halogen. They are in the form of either straight or branched chains and are, for example, fluoromethyl, chloromethyl, fluoroethyl, chloroethyl, trifluoromethyl or trichloromethyl.

The acid addition salts of the compounds of the invention include salts with inorganic or organic acids, for example, hydrochloric, nitric, sulphuric, acetic, 4-toluene-sulphonic or oxalic acids.

The metal complexes of the compounds of the invention include complexes with copper, zinc or manganese cations.

Optional substituents on the phenyl group include halogen, $C_{1-4}$ alkyl, $C_{1-4}$ alkoxy, $C_{1-4}$ haloalkoxy, $C_{2-4}$ alkenyl, $C_{2-4}$ alkynyl, $C_{1-4}$ haloalkyl, phenyl, benzyl, phenoxy or benzyloxy each of phenyl, benzyl, phenoxy and benzyloxy being optionally substituted with halogen, $C_{1-4}$ alkyl, $C_{1-4}$ haloalkyl, $C_{1-4}$ alkoxy or $C_{1-4}$ haloalkoxy.

In one aspect the invention provides a compound of formula (I), wherein $R^1$ is phenyl optionally substituted with halogen, $C_{1-4}$ alkyl, $C_{1-4}$ alkoxy, $C_{1-4}$ haloalkyl, $C_{2-4}$ haloalkoxy, $C_{2-4}$ alkenyl, $C_{1-4}$ alkynyl, phenyl, phenoxy, benzyl or benzyloxy wherein the phenyl, phenoxy, benzyl and benzyloxy moieties are optionally substituted with halogen, $C_{1-4}$ alkyl, $C_{1-4}$ haloalkyl, $C_{1-4}$ alkoxy or $C_{1-4}$ haloalkoxy; $R^2$ and $R^3$ are independently hydrogen or $C_{1-4}$ alkyl; $R^4$, $R^5$ and $R^6$ are independently hydrogen, $C_{1-4}$ alkyl, $C_{1-4}$ haloalkyl or $C_{1-4}$ alkoxy; $R^7$, $R^8$ and $R^9$ are independently hydrogen, halogen, $C_{1-4}$ alkyl, $C_{1-4}$ haloalkyl or $C_{1-4}$ alkoxy; and acid addition salts or metal complexes thereof.

In a further aspect the invention provides a compound of formula (I), wherein $R^1$ is phenyl optionally substituted with halogen, $C_{1-4}$ alkyl (especially methyl), $C_{1-4}$ alkoxy (especially methoxy), $C_{1-4}$ haloalkyl (especially trifluoromethyl) or $C_{1-4}$ haloalkoxy (especially trifluoromethoxy); $R^2$ and $R^3$ are independently hydrogen or $C_{1-4}$ alkyl (especially methyl); $R^4$ is hydrogen, $C_{1-4}$ alkyl (especially methyl) or $C_{1-4}$ alkoxy (especially methoxy), $R^5$, $R^6$, $R^8$ and $R^9$ are hydrogen; $R^7$ is hydrogen or $C_{1-4}$ alkyl (especially methyl); and acid addition salts or metal complexes thereof.

In a still further aspect the invention provides a compound of formula (I), wherein $R^1$ is phenyl optionally substituted with halogen, $C_{1-4}$ alkyl, $C_{1-4}$ alkoxy, $C_{1-4}$ haloalkyl or $C_{1-4}$ haloalkoxy; $R^2$ and $R^3$ are independently hydrogen or methyl; $R^4$, $R^5$, $R^6$, $R^8$ and $R^9$ are all hydrogen; $R^7$ is methyl; and acid addition salts or metal complexes thereof.

In another aspect the invention provides a compound of formula (I), wherein $R^1$ is phenyl optionally substituted with chlorine, fluorine, bromine, methyl, methoxy, trifluoromethyl or trifluoromethoxy; $R^2$ and $R^3$ are independently hydrogen or methyl; $R^4$, $R^5$, $R^6$, $R^8$ and $R^9$ are all hydrogen; $R^7$ is methyl; and acid addition salts or metal complexes thereof.

In one particular aspect the invention provides compounds of formula (I), in which $R^5$, $R^6$, $R^8$ and $R^9$ are all hydrogen, $R^1$ is phenyl or phenyl substituted with one or two halogens (especially chlorine, fluorine or bromine), $C_{1-4}$ alkoxy (especially methoxy), $C_{1-4}$ alkyl (especially methyl), $C_{1-4}$ haloalkyl (especially trifluoromethyl) or $C_{1-4}$ haloalkoxy (especially trifluoromethoxy), $R^2$, $R^3$ and $R^4$, which are the same or different, are hydrogen or $C_{1-4}$ alkyl (especially methyl) and $R^7$ is $C_{1-4}$ alkyl (especially methyl).

Examples of compounds of the invention of formula (I) are given in Table I.

TABLE I

| Compound No | $R^1$ | $R^2$ | $R^3$ | $R^4$ | $R^5$ | $R^6$ | $R^7$ | $R^8$ | $R^9$ | mp °C. |
|---|---|---|---|---|---|---|---|---|---|---|
| 1 | $C_6H_5$ | H | H | H | H | H | $CH_3$ | H | H | oil |
| 2 | 4-Cl—$C_6H_4$ | H | H | H | H | H | $CH_3$ | H | H | oil |
| 3 | 4-F—$C_6H_4$ | H | H | H | H | H | $CH_3$ | H | H | oil |
| 4 | 2,4-$Cl_2$—$C_6H_3$ | H | H | H | H | H | $CH_3$ | H | H | |
| 5 | 2-Cl—$C_6H_4$ | H | H | H | H | H | $CH_3$ | H | H | oil |
| 6 | 4-$CH_3O$—$C_6H_4$ | H | H | H | H | H | $CH_3$ | H | H | |
| 7 | 2-$CH_3O$—$C_6H_4$ | H | H | H | H | H | $CH_3$ | H | H | oil |
| 8 | 3-Cl—$C_6H_4$ | H | H | H | H | H | $CH_3$ | H | H | oil |
| 9 | 4-$CH_3$—$C_6H_4$ | H | H | H | H | H | $CH_3$ | H | H | oil |
| 10 | 4-$CF_3$—$C_6H_4$ | H | H | H | H | H | $CH_3$ | H | H | |
| 11 | 4-$CF_3O$—$C_6H_4$ | H | H | H | H | H | $CH_3$ | H | H | gum |
| 12 | 4-Br—$C_6H_4$ | H | H | H | H | H | $CH_3$ | H | H | |
| 13 | 4-Cl—$C_6H_4$ | $CH_3$ | H | H | H | H | $CH_3$ | H | H | |
| 14 | 4-Cl—$C_6H_4$ | $CH_3$ | $CH_3$ | H | H | H | $CH_3$ | H | H | |
| 15 | $C_6H_5$ | H | H | H | H | H | H | H | H | oil |

TABLE I-continued

| Compound No | R¹ | R² | R³ | R⁴ | R⁵ | R⁶ | R⁷ | R⁸ | R⁹ | mp °C. |
|---|---|---|---|---|---|---|---|---|---|---|
| 16 | 4-Cl—$C_6H_4$ | H | H | H | H | H | H | H | H | |
| 17 | 4-F—$C_6H_4$ | H | H | H | H | H | H | H | H | oil |
| 18 | 2,4-$Cl_2$—$C_6H_3$ | H | H | H | H | H | H | H | H | |
| 19 | 2-Cl—$C_6H_4$ | H | H | H | H | H | H | H | H | oil |
| 20 | 4-$CH_3O$—$C_6H_4$ | H | H | H | H | H | H | H | H | |
| 21 | 2-$CH_3O$—$C_6H_4$ | H | H | H | H | H | H | H | H | |
| 22 | 3-Cl—$C_6H_4$ | H | H | H | H | H | H | H | H | oil |
| 23 | 4-$CH_3$—$C_6H_4$ | H | H | H | H | H | H | H | H | oil |
| 24 | 4-$CF_3$—$C_6H_4$ | H | H | H | H | H | H | H | H | |
| 25 | 4-$CF_3O$—$C_6H_4$ | H | H | H | H | H | H | H | H | |
| 26 | 4-Br—$C_6H_4$ | H | H | H | H | H | H | H | H | |
| 27 | 4-Cl—$C_6H_4$ | $CH_3$ | H | H | H | H | H | H | H | |
| 28 | 4-Cl—$C_6H_4$ | $CH_3$ | $CH_3$ | H | H | H | H | H | H | |
| 29 | $C_6H_5$ | H | H | $CH_3$ | H | H | H | H | H | |
| 30 | $C_6H_5$ | $CH_3$ | H | H | H | H | $CH_3$ | H | H | oil |
| 31 | 2-$CH_3$—$C_6H_4$ | H | H | H | H | H | $CH_3$ | H | H | oil |
| 32 | 3-$CH_3$—$C_6H_4$ | H | H | H | H | H | $CH_3$ | H | H | oil |
| 33* | $C_6H_5$ | H | H | H | H | H | $CH_3$ | H | H | oil |
| 34 | 4-t-$C_4H_9$—$C_6H_4$ | H | H | H | H | H | $CH_3$ | H | H | oil |
| 35 | 4-t-$C_4H_9$—$C_6H_4$ | $CH_3$ | H | H | H | H | $CH_3$ | H | H | oil |
| 36 | $C_6H_5$ | H | H | $CH_3O$ | H | H | $CH_3$ | H | H | 69.6–71.4 |
| 37 | 2-Cl—$C_6H_4$ | H | H | $CH_3O$ | H | H | $CH_3$ | H | H | 99.8–102.1 |
| 38 | 3-$CF_3$—$C_6H_4$ | H | H | H | H | H | $CH_3$ | H | H | gum |
| 39 | 4-$C_6H_5$—$C_6H_4$ | H | H | H | H | H | $CH_3$ | H | H | 101.3–101.9 |
| 40 | 3-$C_6H_5O$—$C_6H_4$ | H | H | H | H | H | $CH_3$ | H | H | gum |
| 41 | 3,4-$(CH_3)_2$—$C_6H_3$ | H | H | H | H | H | $CH_3$ | H | H | |
| 42 | 3,4-$Cl_2$—$C_6H_3$ | H | H | H | H | H | $CH_3$ | H | H | gum |
| 43 | 4-$C_6H_5CH_2O$—$C_6H_4$ | H | H | H | H | H | $CH_3$ | H | H | |
| 44 | 3-$CF_3$—$C_6H_4$ | H | H | H | H | H | H | H | H | |
| 45 | 4-$C_6H_5$—$C_6H_4$ | H | H | H | H | H | H | H | H | |
| 46 | 3-$C_6H_5O$—$C_6H_4$ | H | H | H | H | H | H | H | H | |
| 47 | 3,4-$(CH_3)_2$—$C_6H_3$ | H | H | H | H | H | H | H | H | |
| 48 | 3,4-$Cl_2$—$C_6H_3$ | H | H | H | H | H | H | H | H | |
| 49 | 4-$C_6H_5CH_2O$—$C_6H_4$ | H | H | H | H | H | H | H | H | |
| 50 | 2-Cl—$C_6H_4$ | $CH_3$ | H | H | H | H | $CH_3$ | H | H | |
| 51 | 2-Cl—$C_6H_4$ | H | H | H | H | H | H | H | H | |
| 52 | 2-Cl—$C_6H_4$ | $CH_3$ | $CH_3$ | H | H | H | $CH_3$ | H | H | |
| 53 | 2-Cl—$C_6H_4$ | $CH_3$ | $CH_3$ | H | H | H | H | H | H | |

*$ZnCl_2$ complex of compound No 1

TABLE II

SELECTED PROTON NMR DATA

Table II shows selected proton NMR data for certain compounds described in Table I and characterised therein as oils or gums. Chemical shifts are measured in ppm from tetramethylsilane, and deuterochloroform was used as a solvent throughout.

| Compound No | NMR DATA |
|---|---|
| 1 | 2.65(3H, s); 4.40(2H, s); 7.05(1H, d); 7.15(1H, d); 7.30(5H, m); 7.70(1H, t); 8.30(1H, d); 8.80(1H, d). |
| 2 | 2.65(3H, s); 4.35(2H, s); 7.05(1H, d); 7.25(4H, m); 7.70(1H, t); 8.30(1H, d); 8.80(1H, d). |
| 3 | 2.67(3H, s); 4.37(2H, s); 7.00(2H, t); 7.05(1H, d); 7.17(1H, d); 7.25(2H, m); 7.72(1H, d); 8.30(1H, d); 8.80(1H, d); |
| 5 | 2.65(3H, s); 4.56(2H, s); 7.00(1H, d); 7.15–7.45(5H, m); 7.71(1H, t); 8.33(1H, d); 8.80(1H, d). |
| 7 | 2.67(3H, s); 3.80(3H, s); 4.42(2H, s); 6.89–6.94(2H, m); 7.03(1H, d); 7.17(1H, d); 7.19–7.30(2H, m); 7.68(1H, t); 8.28(1H, d); 8.80(1H, d). |
| 8 | 2.66(3H, s); 4.37(2H, s); 7.09(1H, d); 7.15–7.30(4H, m); 7.18(1H, d); 7.75(1H, t); 8.34(1H, d); 8.81(1H, d). |
| 9 | 2.33(3H, s); 2.66(3H, s); 4.37(2H, s); 7.08(1H, d); 7.10–7.23(5H, m); 7.70(1H, t); 8.30(1H, d); 8.79(1H, d). |
| 11 | 2.65(3H, s); 4.40(2H, s); 7.10(1H, d); 7.15(3H, t); 7.35(2H, d); 7.75(1H, t); 8.35(1H, d); 8.80(1H, d). |
| 15 | 4.40(2H, s); 7.10(1H, d); 7.20–7.36(6H, m); 7.72(1H, t); 8.34(1H, d); 8.95(2H, d). |
| 17 | 4.35(2H, s); 7.0(2H, t); 7.10(1H, d); 7.30(3H, m); 7.75(1H, t); 8.35(1H, d); 8.95(2H, d). |
| 19 | 4.55(2H, s); 7.04(1H, d); 7.18–7.45(5H, m); 7.75(1H, t); 8.36(1H, d); 8.95(2H, d). |
| 22 | 4.40(2H, s); 7.10(1H, d); 7.25(5H, m); 7.75(1H, t); 8.35(1H, d); 8.95(2H, d). |
| 23 | 2.32(3H, s); 4.35(2H, s); 7.12(3H, d); 7.18(2H, d); 7.28(1H, t); 7.70(1H, t); 8.33(1H, d); 8.92(2H, d). |
| 30 | 1.77(3H, d); 2.65(3H, s); 4.63(1H, q); 7.11(1H, d); 7.16(1H, d); 7.30(5H, m); 7.70(1H, t); 8.27(1H, d); 8.81(1H, d). |
| 31 | 2.28(3H, s); 2.67(3H, s); 4.42(2H, s); 6.90(1H, d); 7.17–7.24(5H, m); 7.69(1H, t); 8.30(1H, d); 8.81(1H, d). |
| 32 | 2.32(3H, s); 2.67(3H, s); 4.37(2H, s); 7.01–7.25(6H, m); 7.70(1H, t); 8.31(1H, d); 8.80(1H, d). |
| 33 | 3.03(3H, s); 4.68(2H, s); 7.30–7.42(6H, m); 7.52(1H, d); 8.03(1H, t); 8.67(1H, d); 8.95(1H, d). |
| 34 | 1.30(9H, s); 2.65(3H, s); 4.38(2H, s); 7.10(1H, d); 7.16(1H, d); 7.29(4H, q); 7.70(1H, t); 8.30(1H, d); 8.80(1H, d). |
| 35 | 1.30(9H, s); 1.74(3H, d); 2.64(3H, s); 4.60(1H, q); 7.14(1H, d); 7.17(1H, d); 7.31(4H, dd); 7.71(1H, t); 8.26(1H, d); 8.82(1H, d). |
| 36 | 2.61(3H, s); 3.81(3H, s); 4.38(2H, s); 7.08(1H, d); 7.13(1H, d); 7.25(5H, m); 8.38(1H, d); 8.75(1H, d). |
| 37 | 2.54(3H, s); 3.72(3H, s); 4.41(2H, s); 6.80(1H, dd); 6.95(2H, m); 7.02(1H, d); 7.19(1H, d); 7.28(1H, dd); 8.37(1H, d); 8.67(1H, d). |
| 38 | 2.65(3H, s); 4.45(2H, s); 7.10(1H, d); 7.20(1H, d); 7.50(3H, m); 7.60(1H, s); 7.75(1H, t); 8.35(1H, d); 8.90(1H, d). |
| 39 | 2.65(3H, s); 4.45(2H, s); 7.15(2H, m); 7.40(5H, m); 7.55(4H, m); 7.75(1H, t); 8.35(1H, d); 8.80(1H, d). |
| 40 | 2.65(3H, s); 4.35(2H, s); 6.85(1H, d); 7.10(7H, m); |

TABLE II-continued
SELECTED PROTON NMR DATA

Table II shows selected proton NMR data for certain compounds described in Table I and characterised therein as oils or gums. Chemical shifts are measured in ppm from tetramethylsilane, and deuterochloroform was used as a solvent throughout.

| Compound No | NMR DATA |
| --- | --- |
|  | 7.30(3H, m); 7.75(1H, t); 8.30(1H, d); 8.80(1H, d). |
| 42 | 2.65(3H, s); 4.35(2H, s); 7.15(3H, m); 7.40(2H, m); 7.75(1H, t); 8.35(1H, d); 8.80(1H, d). |

The following abbreviations are used:
br = broad
s = singlet
d = doublet
dd = double doublet
t = triplet
q = quartlet
m = multiplet Compounds of formula (I), wherein $R^1$, $R^2$, $R^3$, $R^4$, $R^5$, $R^6$, $R^7$, $R^8$ and $R^9$ are as defined above, can be prepared by treating a picoline amidine, or a salt thereof, of general formula (II), wherein $R^1$, $R^2$, $R^3$, $R^4$, $R^5$ and $R^6$ are as defined above, with a β-oxoacetal of general formula (III), wherein $R^7$ and $R^8$ are defined above and $R^{10}$ is $C_{1-4}$ alkyl, to make a compound of formula (I) in which $R^9$ is hydrogen; or with a β-diketone of general formula (IV), wherein $R^7$ and $R^8$ are as defined above and $R^9$ is $C_{1-4}$ alkyl, to make a compound of formula (I) in which $R^9$ is $C_{1-4}$ alkyl; in the presence of a base such as an alkali metal alkoxide (e.g. sodium methoxide or sodium ethoxide) or an organic base (e.g. triethylamine or pyridine). Salts of the picoline amidine can be either hydrochloride, hydrobromide, nitrate, acetate or formate. The reaction is usually carried out in an inert solvent such as ethanol, tetrahydrofuran, pyridine or N,N-dimethylformamide at temperatures of 50°–200° C.

The picoline amidines of general formula (II) can be prepared by reacting a pyridyl imino ether of general formula (V), wherein $R^1$, $R^2$, $R^3$, $R^4$, $R^5$ and $R^6$ are as defined above and $R^{11}$ is $C_{1-4}$ alkyl, with ammonia or an ammonium salt, such as ammonium chloride or ammonium bromide, in a suitable solvent, such as methanol or ethanol, at a temperature of 20°–70° C.

The pyridyl imino ethers of general formula (V) can be prepared by reacting a pyridyl nitrile of general formula (VI), wherein $R^1$, $R^2$, $R^3$, $R^4$, $R^5$ and $R^6$ are as defined above, with an alkali metal alkoxide of general formula (VII), wherein $R^{11}$ is as defined above and M is sodium or potassium (the alkali metal alkoxide of general formula (VII) is, for example, sodium methoxide or sodium ethoxide), in a suitable solvent, such as methanol or ethanol, at a temperature of 20°–50° C.

The pyridyl nitriles of general formula (VI) can be prepared by reacting a pyridine N-oxide of general formula (VIII), wherein $R^1$, $R^2$, $R^3$, $R^4$, $R^5$ and $R^6$ are as defined above, with trimethylsilylcyanide (TMSCN) or potassium cyanide and dimethyl sulphate in a suitable solvent, such as acetonitrile or N,N-dimethylformamide, at a temperature of 20°–50° C.

The pyridine N-oxides of general formula (VIII) can be prepared by oxidation of substituted pyridines of general formula (IX), wherein $R^1$, $R^2$, $R^3$, $R^4$, $R^5$ and $R^6$ are as defined above, with an oxidising agent such as hydrogen peroxide or an organic peroxyacid (for example meta-chloroperbenzoic acid or monoperoxyphthalic acid magnesium salt hexahydrate) in a suitable solvent, such as acetic acid, chloroform or methylene chloride, and at a suitable temperature.

The substituted pyridines of general formula (IX) are prepared by methods set out in the literature.

In an alternative process, compounds of the general formula (I) in which $R^1$, $R^2$, $R^3$, $R^4$, $R^5$, $R^6$, $R^7$ and $R^8$ are as defined above and $R^9$ is hydrogen, can be prepared by the reductive dehalogenation of a halopyrimidine of general formula (X), wherein $R^1$, $R^2$, $R^3$, $R^4$, $R^5$, $R^6$, $R^7$ and $R^8$ are as defined above and X is a halogen (for example chlorine or bromine). The dehalogenation reaction can be carried out with hydrogen in the presence of a suitable catalyst, such as palladium on carbon, in a convenient inert solvent, such as water, methanol, ethanol or ethyl acetate, at a suitable temperature.

The halopyrimidines of general formula (X) can be prepared by halogenating hydroxypyrimidines of general formula (XI), wherein $R^1$, $R^2$, $R^3$, $R^4$, $R^5$, $R^6$, $R^7$ and $R^8$ are as defined above, with a suitable halogenating agent, such as phosphorus trichloride or tribromide, phosphorus pentachloride or pentabromide, and phosphorus oxychloride or oxybromide, at a suitable temperature.

The hydroxypyrimidines of general formula (XI) can be prepared by reacting a picoline amidine of general formula (II) with a β-ketoester of general formula (XII), wherein $R^7$, $R^8$ and $R^{10}$ are as defined above, in the presence of a base, such as an alkali metal alkoxide (for example sodium methoxide or sodium ethoxide) or an organic base (for example, triethylamine or pyridine), at a suitable temperature.

The compounds of the general formula (I) in which $R^1$, $R^2$, $R^3$, $R^4$, $R^5$, $R^6$, $R^7$ and $R^8$ are as defined above and $R^9$ is $C_{1-4}$ alkoxy, can be prepared by reacting the halopyrimidines of general formula (X), with an alkali metal alkoxide (VII) in a suitable solvent, such as methanol or ethanol, at a temperature of 20°–70° C.

In a further variation of the process, compounds of general formula (I) in which $R^1$, $R^2$, $R^3$, $R^4$, $R^5$, $R^6$, $R^7$, $R^8$ and $R^9$ are as defined above, can be prepared by coupling together a bromopyridine of general formula (XIII), wherein $R^1$, $R^2$, $R^3$, $R^4$, $R^5$ and $R^6$ are as defined above, with a bromopyrimidine of general formula (XIV), wherein $R^7$, $R^8$ and $R^9$ are as defined above. The coupling reaction can be carried out by treating the bromopyridine (XIII) with normal butyl lithium in tetrahydrofuran followed by zinc chloride in diethylether, and then adding a solution of tetrakis(triphenylphosphine)palladium(O) and the bromopyrimidine (XIV). The reaction is carried out at temperatures of between −100° and +65° C.

In a further alternative process, compounds of the general formula (I) in which $R^1$, $R^2$, $R^3$, $R^4$, $R^5$, $R^6$, $R^7$, $R^8$ and $R^9$ are as defined above, can be prepared by coupling together a bromopyridine of general formula (XV), wherein $R^4$, $R^5$, $R^6$, $R^7$, $R^8$ and $R^9$ are as defined above, with a benzyl halide of general formula (XVI) wherein $R^1$, $R^2$, $R^3$ are as defined above, and X is a halogen (for example chlorine or bromine). The coupling reaction can be carried out by treating the benzyl halide (XVI) with magnesium (in the presence of a suitable solvent, for example diethylether or tetrahydrofuran), followed by zinc chloride in tetrahydrofuran or diethylether, and then adding the bromopyridine (XV) plus tetrakis(triphenylphosphine)palladium(O) in a suitable solvent, at a suitable temperature. Alternatively, the coupling reaction can be carried out by treating the bromopyridine (XV) with normal butyl lithium in tetrahydrofuran, followed by zinc chloride in diethylether or tetrahydrofuran, and then adding the benzyl halide (XVI) plus tetrakis(triphenylphosphine)palladium (O) in a suitable solvent, at a suitable temperature.

In another alternative process, compounds of the general formula (I) in which $R^1$, $R^2$, $R^3$, $R^4$, $R^5$, $R^6$, $R^7$, $R^8$ and $R^9$ are as defined above, can be prepared by coupling together a bromopyridine of general formula (XV), wherein $R^4$, $R^5$, $R^6$, $R^7$, $R^8$ and $R^9$ are as defined above, with a substituted toluene of general formula (XVII), wherein $R^1$, $R^2$ and $R^3$ are as defined above. The coupling reaction can be carried out by treating the substituted toluene (XVII) with normal butyl lithium in tetramethylethylenediamine (TMEDA) followed by zinc chloride in tetrahydrofuran or diethyl ether, and then adding a solution of tetrakis(triphenylphosphine)-palladium (O) and the bromopyridine (XV). The reaction is carried out at temperatures of between $-80°$ and $70°$ C.

The bromopyridines (XIII) and (XV), bromopyrimidines (XIV) and benzyl halides (XVI) are prepared by methods set out in the literature.

The salts of compounds of general formula (I) can be prepared by adding one equivalent of a strong acid such as hydrochloric acid, sulphuric acid or nitric acid, to a solution of (I) in a suitable solvent.

The present invention includes processes for preparing the compounds of formula (I) as herein defined and intermediates of formula (II), (V), (VI), (VIII), (IX), (X), (XI), (XIII), and (XV) as herein before defined.

The compounds of the invention are active fungicides and may be used to control one or more of the following pathogens: *Pyricularia oryzae* on rice. *Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants. *Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines. Helminthosporium spp., Rhynchosporium spp., Septoria spp., Pyrenophora spp., *Pseudocercosporella herpotrichoides* and *Gaeumannomyces graminis* on cereals. *Cercospora arachidicola* and *Cercosporidium personata* on peanuts and other Cercospora species on other hosts, for example, sugar beet, bananas, soya beans and rice. *Botrytis cinerea* (grey mould) on tomatoes, strawberries, vegetables, vines and other hosts. Alternaria spp. on vegetables (e.g. cucumber), oil-seed rape, apples, tomatoes and other hosts. *Venturia inaequalis* (scab) on apples. *Plasmopara viticola* on vines. Other downy mildews such as *Bremia lactucae* on lettuce, Peronospora spp. on soybeans, tobacco, onions and other hosts, *Pseudoperonospora humuli* on hops and *Pseudoperonospora cubensis* on cucurbits. *Phytophthora infestans* on potatoes and tomatoes and other Phytophthora spp. on vegetables, strawberries, avocado, pepper, ornamentals, tobacco, cocoa and other hosts. *Thanatephorus cucumeris* on rice and other Rhizoctonia species on various hosts such as wheat and barley, vegetables, cotton and turf.

Some of the compounds show a broad range of activities against fungi in vitro. They may also have activity against various post-harvest diseases of fruit (e.g. *Penicillium digitatum* and italicum and *Trichoderma viride* on oranges, *Gloeosporium musarum* on bananas and *Botrytis cinerea* on grapes).

Further, some of the compounds may be active as seed dressings against pathogens including Fusarium spp., Septoria spp., Tilletia spp., (bunt, a seed-borne disease of wheat), Ustilago spp. and Helminthosporium spp. on cereals, *Rhizoctonia solani* on cotton and *Pyricularia oryzae* on rice.

The compounds may move acropetally/locally in plant tissue. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium dodecylbenzenesulphonate, sodium, calcium or ammonium lignosulphonate, butylnaphthalene sulphonate, and a mixture of sodium diisopropyl- and triisopropyl- naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil-borne diseases and downy and powdery mildews on grapes and powdery mildew and scab on apple, etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are (RS)-1-aminopropylphosphonic acid, (RS)-4-(4-chlorophenyl)-2-phenyl-2-(1H̄-1,2,4-triazol-1-yl-methyl)butyronitrile, (Z)-N-but-2-enyloxymethyl-2-chloro-2',6'-diethylacetanilide, 1-(2-cyano-2-methoxyimino-acetyl)-3-ethyl urea, 1-[(2RS,4RS;2RS,4RS)-4-bromo-2-(2,4-dichlorophenyl)tetrahydrofuryl]-1H̄-1,2,4-tri-azole, 3-(2,4-dichlorophenyl)-2-(1H̄-1,2,4-triazol-1-yl)-quinazolin-4(3H̄)-one, 3-chloro-4-[4-methyl-2-(1H̄-1,2,4-triazol-1-methyl)-1,3-dioxolan-2-yl]phenyl-4-chlorophenyl ether, 4-bromo-2-cyano-N,N-dimethyl-6-trifluoromethylbenz-imidazole-1-sulphonamide, 5-ethyl-5,8-dihydro-8-oxo(1,3)dioxolo(4,5-g)quinoline-7-carboxylic acid, α-[N-(3-chloro-2,6-xylyl)-2-methoxyacetamido]-γ-butyrolactone, aldimorph, anilazine, benalaxyl, benomyl, biloxazol, binapacryl, bitertanol, blasticidin S, bupirimate, buthiobate, captafol, captan, carbendazim, carboxin, chlorbenz-thiazone, chloroneb, chlorothalonil, chlorozolinate, copper containing compounds such as copper oxychloride, copper sulphate and Bordeaux mixture, cycloheximide, cymoxanil, cyproconazole, cyprofuram, di-2-pyridyl disulphide 1,1'-dioxide, dichlofluanid, dichlone, diclobutrazol, diclomezine, dicloran, difenoconazole, dimethamorph, dimethirimol, diniconazole, dinocap, ditalimfos, dithianon, dodemorph, dodine, edifenphos, etaconazole, ethirimol, ethyl (Z)-N-benzyl-N-([methyl(methylthioethylideneamino-oxycarbonyl)amino]thio)-β-alaninate, etridiazole, fenapanil, fenarimol, fenfuram, fenpiclonil, fenpropidin, fenpropimorph, fentin acetate, fentin hydroxide, flutolanil, flutriafol, flusilazole, folpet, fosetyl-aluminium, fuberidazole, furalaxyl, furconazole-cis, guazatine, hexaconazole, hydroxyisoxazole, imazalil, imibenconazole, iprobenfos, iprodione, isoprothiolane, kasugamycin, mancozeb, maneb, mepanipyrim, mepronil, metalaxyl, methfuroxam, metsulfovax, myclobutanil, N-(4-methyl-6-prop-1-ynylpyrimidin-2-yl)aniline, neoasozin, nickel dimethyldithiocarbamate, nitrothal-isopropyl, nuarimol, ofurace, organomercury compounds, oxadixyl, oxycarboxin, pefurazoate, penconazole, pencycuron, phenazin oxide, phthalide, polyoxin D, polyram, probenazole, prochloraz, procymidone, propamocarb, propiconazole, propineb, prothiocarb, pyrazophos, pyrifenox, pyroquilon, pyroxyfur, pyrrolnitrin, quinomethionate, quintozene, SSF-109, streptomycin, sulphur, tebuconazole, techlofthalam, tecnazene, tetraconazole, thiabendazole, thicyofen, thiophanate-methyl, thiram, tolclofos-methyl, triacetate salt of 1,1'-iminodi(octamethylene)diguanidine, triadimefon, triadimenol, triazbutyl, tricyclazole, tridemorph, triforine, validamycin A, vinclozolin, zarilamid and zineb. The compounds of general formula (I) can be mixed with soil, peat or other rooting media for the protection of plants against seed-borne, soil-borne or foliar fungal diseases.

Suitable insecticides which may be incorporated in the composition of the invention include buprofezin, carbaryl, carbofuran, carbosulfan, chlorpyrifos, cycloprothrin, demeton-s-methyl, diazinon, dimethoate, ethofenprox, fenitrothion, fenobucarb, fenthion, formothion, isoprocarb, isoxathion, monocrotophos, phenthoate, pirimicarb, propaphos and XMC.

Plant growth regulating compounds are compounds which control weeds or seedhead, formation, or selectively control the growth of less desirable plants (e.g. grasses).

Examples of suitable plant growth regulating compounds for use with the invention compounds are 3,6-dichloropicolinic acid, 1-(4-chlorophenyl)-4,6-dimethyl-2-oxo-1,2-dihydropyridine-3-carboxylic acid, methyl-3,6-dichloroanisate, abscisic acid, asulam, benzoylprop-ethyl, carbetamide, daminozide, difenzoquat, dikegulac, ethephon, fenpentezol, fluoridamid, glyphosate, glyphosine, hydroxybenzonitriles (e.g. bromoxynil), inabenfide, isopyrimol, long chain fatty alcohols and acids, maleic hydrazide, mefluidide, morphactins (e.g. chlorfluoroecol), paclobutrazol, phenoxyacetic acids (e.g. 2,4-D or MCPA), substituted benzoic acid (e.g. triiodo-benzoic acid), substituted quaternary ammonium and phosphonium compounds (e.g. chloromequat, chlorphonium or mepiquatchloride), tecnazene, the auxins (e.g. indoleacetic acid, indolebutyric acid, naphthylacetic acid or naphthoxyacetic acid), the cytokinins (e.g. benzimidazole, benzyladenine, benzylaminopurine, diphenylurea or kinetin), the gibberellins (e.g. $GA_3$, $GA_4$ or $GA_7$) and triapenthenol.

The following examples illustrate the invention. Throughout the examples, reactions involving air-sensitive intermediates were performed under atmospheres of nitrogen. Unless otherwise stated, chromatography was performed using silica gel as the stationary phase.

HYFLO, DISPERSOL and TWEEN, where used in the examples, are Trade or Service Marks.

EXAMPLE 1

This example illustrates the preparation of 2-(6-benzyl-2-pyridyl)-4-methylpyrimidine (Compound No 1 in Table 1).

Stage 1

A solution of 2-benzylpyridine (10.0 g, 0.059 moles) and hydrogen peroxide (33% w/v, 4.02 g, 12.2 ml, 0.118 moles) in glacial acetic acid (40 ml) was heated at 60° C. for 17 hours. The reaction mixture was cooled to room temperature, the acetic acid evaporated under reduced pressure and the residue dissolved in chloroform. After neutralisation with potassium carbonate (20 g) the chloroform was removed to give 2-benzylpyridine-N-oxide (10.86 g, 99%) as a viscous oil which crystallised on standing.

Stage 2

Trimethylsilyl cyanide (14.56 g, 19.6 ml, 0.147 moles) was added dropwise to a solution of 2-benzylpyridine-N-oxide (10.86 g, 0.059 moles) and triethylamine (8.91 g, 12.3 ml, 0.088 moles) in acetonitrile (40 ml) at 20° C. After complete addition the mixture was heated under reflux for 20 hours, cooled to room temperature and partitioned between methylene chloride and saturated sodium bicarbonate. The organic layer was washed with water and saturated sodium chloride, and then dried over anhydrous magnesium sulphate. Removal of the solvent gave an orange oil which was purified by column chromatography (silica gel eluted with hexane:ethyl acetate 9:1) to give 2-benzyl-6-cyanopyridine (1.84 g, 16%) as a pale yellow oil.

Stage 3

2-Benzyl-6-cyanopyridine (0.84 g, 0.0043 moles) was added to a solution of sodium methoxide in methanol [prepared by dissolving sodium metal (0.11 g, 0.0047 gram atoms) in methanol (10 ml)] and the mixture stirred at 20° C. for 5 hours. The methanol was evaporated, the residue taken up in chloroform and the precipitate filtered off through a silica bed. Removal of the solvent from the filtrate gave methyl 6-benzyl-2-picoline imidate (0.81 g, 84%) which was used in the next stage without further purification.

Stage 4

A mixture of methyl 6-benzyl-2-picoline imidate (0.81 g, 0.0036 moles) and ammonium chloride (0.21 g, 0.0039 moles) in ethanol (9 ml) was refluxed for 5 hours. The ethanol was removed in vacuo to give 6-benzyl-2-picoline amidine hydrochloride which was used in the final stage without further purification.

Stage 5

A mixture of the crude 6-benzyl-2-picoline amidine hydrochloride (0.89 g, 0.0036 moles) from the previous stage, sodium ethoxide (0.24 g, 0.0036 moles) and 4,4-dimethoxy-2-butanone (0.53 g, 0.0036 moles) in ethanol (10 ml) was refluxed for 5 hours. The ethanol was evaporated; the residue dissolved in chloroform, washed with water and dried over anhydrous magnesium sulphate. Removal of the solvent gave a dark brown oil which was purified by column chromatography (silica gel eluted with methylene chloride:tetrahydrofran 9:1) to give the title compound (0.100 g, 11%) as a brown oil ($M^+$ 261).

EXAMPLE 2

This example illustrates the preparation of 2-(6-p-chlorobenzyl-2-pyridyl)-4-methylpyrimidine (Compound No 2 in Table 1).

Stage 1

A solution of 2-p-chlorobenzylpyridine (12.0 g, 0.059 moles) and hydrogen peroxide (33% w/v, 4.02 g, 12.2 ml, 0.118 moles) in glacial acetic acid (40 ml) was heated at 60° for 15 hours. The reaction mixture was cooled to room temperature, the acetic acid evaporated under reduced pressure and the residue dissolved in chloroform. After neutralisation with potassium carbonate (20 g) the chloroform was removed to give 2-p-chlorobenzylpyridine-N-oxide (11.02 g, 85%) as a viscous oil.

Stage 2

Trimethylsilyl cyanide (12.42 g, 16.7 ml, 0.125 moles) was added dropwise to a solution of 2-p-chlorobenzyl-pyridine-N-oxide (11.0 g, 0.05 moles) and triethylamine (7.61 g, 10.5 ml, 0.075 moles) in acetronitrile (40 ml) at 20° C. After complete addition the mixture was heated under reflux for 48 hours, cooled to room temperature and partitioned between methylene chloride and saturated sodium bicarbonate. The organic layer was washed with water and saturated sodium chloride and dried over anhydrous magnesium sulphate. Removal of the solvent gave a brown oil which was purified by column chromatography (silica gel eluted with hexane:ethyl acetate 9:1) to give 2-p-chlorobenzyl-6-cyanopyridine (1.69 g, 15%) as a pale yellow oil.

Stage 3

2-p-Chlorobenzyl-6-cyanopyridine (1.69 g, 0.0074 moles) was added to a solution of sodium methoxide [prepared by dissolving sodium metal (0.19 g, 0.0081 gram atoms) in methanol (20 ml)] under nitrogen, and the mixture stirred at 20° C. for 17 hours. The methanol was evaporated, the residue taken up in chloroform, neutralised with acetic acid and the precipitate filtered off on HYFLO. Concentration of the filtrate gave methyl 6-p-chlorobenzyl-2-picoline imidate (1.20 g, 62%) which was used in the next stage without further purification.

Stage 4

A mixture of methyl 6-p-chlorobenzyl-2-picoline imidate (1.2 g, 0.00046 moles) and ammonium chloride (0.27 g, 0.0051 moles) in ethanol (10 ml) was refluxed for 6 hours. Removal of the ethanol in vacuo gave 6-p-chlorobenzyl-2-picoline amidine hydrochloride which was used in the final stage without further purification.

Stage 5

A mixture of the crude 6-p-chlorobenzyl-2-picoline amidine hydrochloride (1.20 g, 0.0046 moles) from the previous stage, sodium ethoxide (0.31 g, 0.0046 moles) and 4,4-dimethoxy-2-butanone (0.68 g, 0.0046 moles) in ethanol (10 ml) was refluxed for 5 hours. The ethanol was evaporated; the residue dissolved in chloroform, washed with water and dried over anhydrous magnesium sulphate. Removal of the solvent gave a brown oil which was purified by column chromatography (silica gel eluted with tetrahydrofuran:methylene chloride 3:97) to give the title compound (0.38 g, 28%) as a yellow oil (M+ 295).

EXAMPLE 3

This example illustrates the preparation 2-(6-o-chlorobenzyl-2-pyridyl)-4-methylpyrimidine (Compound No 5 in Table I).

Stage 1

The Grignard reagent, generated from o-chlorobenzyl chloride (52.0 g, 0.32 moles) and magnesium turnings (8.4 g, 0.35 g atoms) in dry diethyl ether (350 ml), was added dropwise to a refluxing solution of 2-bromopyridine (34.2 g, 0.22 moles) and tetrakis(triphenylphosphine)palladium (0) (5.0 g) in dry diethyl ether (200 ml) under a nitrogen atmosphere. A white precipitate was produced and the reaction mixture was heated at reflux for 1 hour. After cooling to room temperature, 1N hydrochloric acid was added carefully to dissolve the white solid and the ether layer separated off. The ethereal extract was washed with 1N hydrochloric acid, neutralised with 2N sodium hydroxide solution, washed with water and dried over anhydrous magnesium sulphate. Removal of the solvent gave an orange oil which was purified by column chromatography (silica gel eluted with tetrahydrofuran:chloroform 5:95) to give 2-(o-chlorobenzyl)-pyridine (32 g, 73%) as a pale yellow oil.

Stage 2

A solution of 2-(o-chlorobenzyl)pyridine (32 g, 0.16 moles) and hydrogen peroxide (30% w/v, 10.7 g, 36.0 ml, 0.31 moles) in glacial acetic acid (100 ml) was heated at 75° C. for 17 hours. The reaction mixture was cooled to room temperature, the acetic acid evaporated under reduced pressure and the residue dissolved in chloroform. After neutralisation with potassium carbonate (30 g) the chloroform was removed to give 2-(o-chlorobenzyl)pyridine-N-oxide (34.4 g, 100%) as a viscous oil.

Stage 3

Trimethylsilyl cyanide (36.15 g, 48.6 ml, 0.36 moles) was added dropwise to a solution of 2-(o-chlorobenzyl)-pyridine-N-oxide (32.0 g, 0.15 moles) and triethylamine (22.13 g, 30.5 ml, 0.22 moles) in acetonitrile (100 ml) at 20° C. under a nitrogen atmosphere. After complete addition the reaction mixture was heated under reflux for 48 hours, cooled to room temperature and partitioned between methylene chloride and saturated sodium bicarbonate solution. The organic layer was washed with water and saturated sodium chloride solution and was then dried over anhydrous magnesium sulphate. Removal of the solvent gave an orange brown oil which was purified by column chromatography (silica gel eluted with hexane:ethyl acetate 4:1) to give 2-(o-chlorobenzyl)-6-cyanopyridine (11.5 g, 35%) as a pale yellow oil.

Stage 4

2-(o-Chlorobenzyl)-6-cyanopyridine (5.0 g, 0.022 moles) was added to a solution of sodium methoxide in methanol [prepared by dissolving sodium metal (0.55 g, 0.024 g atoms) in methanol (50 ml)] and the mixture stirred at 20° C. for 5 hours. The methanol was evaporated, the residue taken up in dichloromethane and the precipitate filtered off through a silica bed. Removal of the solvent from the filtrate gave methyl 6-(o-chlorobenzyl)-2-picoline imidate (5.5 g, 100%) as a brown oil which was used in the next stage without further purification.

Stage 5

A mixture of methyl 6-(o-chlorobenzyl)-2-picoline imidate 5.5 g, 0.021 moles) and ammonium chloride (1.28 g, 0.024 moles) in ethanol (40 ml) was refluxed for 4 hours. The ethanol was removed in vacuo to give 6-(o-chlorobenzyl)-2-picoline amidine hydrochloride which was used in the final stage without further purification.

Stage 6

A mixture of the crude 6-(o-chlorobenzyl)-2-picoline amidine hydrochloride (5.95 g, 0.021 moles) from the previous stage, sodium ethoxide (1.43 g, 0.0211 moles) and 4,4-dimethoxy-2-butanone (3.10 g, 0.0211 moles) in ethanol (50 ml) was refluxed for 5 hours. The ethanol was evaporated; the residue dissolved in chloroform, washed with water and dried over anhydrous magnesium sulphate. Removal of the solvent gave a dark brown oil which was purified by column chromatography (silica gel eluted with methylene chloride: tetrahydrofuran 98:2) to give the title compound (1.97 g, 32%) as a yellow oil.

EXAMPLE 4

This example illustrates the preparation of 2-(6-p-fluorobenzyl-2-pyridyl)-4-methylpyrimidine (Compound No. 3 in Table I).

Stage 1

A solution of normal butyl lithium (28.6 ml of a 2.5M solution in hexane, 0.0714 moles) was added dropwise to a solution of 2,6-dibromopyridine (15.8 g, 0.067 moles) in dry tetrahydrofuran (100 ml) at −78° C. under a nitrogen atmosphere. The dark green mixture was stirred for 0.5 hours at −78° C. after the addition was complete and a solution of zinc chloride (205 ml of a 1.0M solution in diethyl ether, 0.205 moles) added dropwise so that the temperature was kept below −60° C. A white precipitate formed and the solution was stirred at −78° C. for a further 0.5 hours.

Tetrakis(triphenylphosphine)palladium (O) (1.1 g, 0.00095 moles) was added, followed by 2-bromo-4-methyl-pyrimidine (8.23 g, 0.048 moles) in dry tetrahydrofuran (100 ml), keeping the temperature below −70° C. After complete addition the reaction mixture was refluxed for 4 hours, cooled to room temperature, poured into a 10% solution of sodium ethylenediaminetetraacetate in water and extracted with methylene chloride. The combined methylene chloride extracts were washed, dried and the solvent removed to give a dark oil which was purified by column chromatography (silica gel eluted with t-butyl methyl ether) giving 2-(6-bromo-2-pyridyl)-4-methylpyrimidine (3.6 g, 30%) as a yellow solid. This was used in the next stage without further recrystallisation.

Stage 2

A solution of p-fluorobenzyl chloride (0.87 g, 0.006 moles) in dry diethyl ether (6.0 ml) was added dropwise to magnesium turnings (0.16 g, 0.0064 g atoms) in dry diethyl ether (2.0 ml) at room temperature under a nitrogen atmosphere. After the Grignard reagent had been formed, a solution of zinc chloride (12.0 ml of a 1.0M solution in diethyl ether, 0.012 moles) was added at room temperature, and a dense white precipitate formed. Tetrakis(triphenylphosphine)palladium (O) (0.09 g, 0.00008 moles) was added, followed by 2-(6-bromo-2-pyridyl)-4-methylpyrimidine (1.0 g, 0.004 moles) in dry ether (5 ml) and methylene chloride (5 ml) at 20° C. After complete addition the orange mixture was heated at reflux for 2 hours, cooled to room temperature, poured carefully into 1N hydrochloric acid and extracted with ethyl acetate. The combined ethyl acetate extracts were washed, dried and the solvent removed to give an orange oil which was purified by column chromatography (silica gel eluted with tetrahydrofuran: methylene chloride 2:98) to give the title compound (0.52 g, 47%) as a yellow oil.

EXAMPLE 5

This example illustrates the preparation of 2-(6-α-methylbenzyl-2-pyridyl)-4-methylpyrimidine (Compound No. 30 in Table I).

A solution of normal butyl lithium (3 ml of a 2.5M solution in hexane) was added dropwise to a stirred solution of tetramethylethylenediamine (0.7 ml) in dry ethyl benzene (30 ml) under a nitrogen atmosphere at room temperature. After complete addition the resulting yellow solution was stirred for 1 hour at 20° C. and a solution of zinc chloride (21 ml of 1.0M solution in tetrahydrofuran, 0.021 moles) added dropwise so that the temperature was kept at 20° C. A solution of 2-(6-bromo-2-pyridyl)-4-methylpyrimidine (1.0 g, 0.004 moles) (see Example 4 for preparation) and tetrakis(triphenylphosphine)palladium (O) (0.1 g) in dry tetrahydrofuran (25 ml) was added and the mixture refluxed for 3 hours. The reaction mixture was cooled to room temperature, poured into a 10% solution of sodium ethylenediaminetetraacetate in water and extracted with ethyl acetate. The combined ethyl acetate extracts were washed, dried and the solvent removed to give a brown oil which was purified by high pressure liquid chromatography to give the title compound (0.1 g, 7%) as a yellow oil.

EXAMPLE 6

This example illustrates the preparation of 2-(6-o-methylbenzyl-2-pyridyl)-4-methylpyrimidine (Compound No. 31 in Table I).

A solution of normal butyl lithium (3.2 ml of a 2.5M solution in hexane) was added dropwise to a stirred solution of tetramethylethylenediamine (0.65 ml) in o-xylene (30 ml) under a nitrogen atmosphere at room temperature. After complete addition the resulting orange solution was stirred for 1 hour at room temperature, warmed to 85° C. for 30 minutes and cooled to 40° C. Then a solution of zinc chloride (21 ml of 1.0M solution in tetrahydrofuran, 0.021 moles) was added rapidly to the deep red mixture and the reaction stirred at 20° C. for 30 minutes.

A solution of 2-(6-bromo-2-pyridyl)-4-methylpyrimidine (1.0 g, 0.004 moles) (see Example 4 for preparation) and tetrakis(triphenylphosphine)palladium (O) (0.1 g) in dry tetrahydrofuran (25 ml) was added and the mixture refluxed for 2 hours. The reaction mixture was cooled to room temperature, poured into a 10% solution of sodium ethylenediaminetetraacetate in water and extracted with ethyl acetate. The combined ethyl acetate extracts were washed, dried and the solvent removed to give a yellow oil which was purified by column chromatography (silica gel eluted with ethyl acetate: hexane 3:7) to give the title compound (0.83 g, 75%) as a pale yellow oil.

EXAMPLE 7

This example illustrates the preparation of 2-(6-o-methoxybenzyl-2-pyridyl)-4-methylpyrimidine (Compound No. 7 in Table I).

A solution of normal butyl lithium (3.2 ml of a 2.5M solution in hexane) was added dropwise to a stirred solution of tetramethylethylenediamine (0.65 ml, 0.004 moles) in o-methylanisole (35 ml) under a nitrogen atmosphere at room temperature. After complete addition the resultant orange solution was stirred for 1 hour at room temperature, warmed to 85° C. for 30 minutes and cooled to 40° C. Then a solution of zinc chloride (21 ml of 1.0M solution in tetrahydrofuran, 0.021 moles) was added rapidly to the reaction mixture which was stirred at 20° C. for 30 minutes.

A solution of 2-(6-bromo-2-pyridyl)-4-methylpyrimidine (1.0 g, 0.004 moles) (see Example 4 for preparation) and tetrakis(triphenylphosphine)palladium (O) (0.1 g) in dry tetrahydrofuran (25 ml) was added and the mixture refluxed for 2 hours. The reaction mixture was cooled to room temperature, poured into a 10% solution of sodium ethylenediaminetetraacetate in water and extracted with ethyl acetate. The combined ethyl acetate extracts were washed, dried and the solvent removed to give a yellow oil which was purified by column chromatography (silica gel eluted with ethyl acetate) to give the title compound (0.72 g, 62%) as a pale yellow oil.

EXAMPLE 8

This example illustrates the preparation of 2-(6-m-trifluoromethylbenzyl-2-pyridyl)-4-methylpyrimidine (Compound No. 38 in Table I).

A solution of m-trifluoromethylbenzylchloride (1.6 g, 8 mM) in dry diethylether (25 ml) was added dropwise to magnesium turnings (0.2 g, 8 mM) under nitrogen. External heating using a water bath was necessary to initiate and maintain the reaction. Upon completion of the addition the cloudy yellowish reaction mixture was refluxed for one hour.

After cooling to room temperature, zinc chloride solution (24 ml of a 1M solution in diethylether, 24 mM) was added to the reaction mixture and a white precipitate formed.

To the stirred reaction mixture was added a solution of 2-(6-bromo-2-pyridyl)-4-methylpyrimidine (1.0 g, 4 mM) and tetrakis(triphenylphosphine)palladium (O) (0.1 g) in dry tetrahydrofuran (25 ml). An orange/yellow colour developed. The reaction mixture was refluxed for two hours after which time it was allowed to stand at room temperature overnight and then refluxed for a further three hours. The reaction mixture was then cooled to room temperature and poured into a 10% solution of sodium ethylenediaminetetraacetate (150 ml). (2M NaOH solution was added to the mixture until a pH of 8 was attained.)

The layers were separated and the aqueous layer extracted with ethyl acetate. The organic extracts were combined and evaporated to leave a brown sticky solid which was purified by high pressure liquid chromatography using 5% methanol: 95% ethyl acetate and further purified by flash column chromatography using 10% tetrahydrofuran: 90% dichloromethane to give the title compound (0.055 g).

The following are examples of compositions suitable for agricultural and horticultural purposes which can be formulated from the compounds of the invention. Such compositions form another aspect of the invention. Percentages are by weight.

EXAMPLE 9

An emulsifiable concentrate is made up by mixing and stirring the ingredients until all are dissolved.

| Compound No. 1 of Table I | 10% |
| Benzyl alcohol | 30% |
| Calcium dodecylbenzenesulphonate | 5% |
| Nonylphenolethoxylate (13 moles ethylene oxide) | 10% |

-continued

| Alkyl benzenes | 45% |

EXAMPLE 10

The active ingredient is dissolved in methylene dichloride and the resultant liquid sprayed on to the granules of attapulgite clay. The solvent is then allowed to evaporate to produce a granular composition.

| Compound No. 2 of Table I | 5% |
| Attapulgite granules | 95% |

EXAMPLE 11

A composition suitable for use as a seed dressing is prepared by grinding and mixing the three ingredients.

| Compound No. 1 of Table I | 50% |
| Mineral oil | 2% |
| China clay | 48% |

EXAMPLE 12

A dustable powder is prepared by grinding and mixing the active ingredient with talc.

| Compound No. 1 of Table I | 5% |
| Talc | 95% |

EXAMPLE 13

A suspension concentrate is prepared by ball milling the ingredients to form an aqueous suspension of the ground mixture with water.

| Compound No. 1 of Table I | 40% |
| Sodium lignosulphonate | 10% |
| Bentonite Clay | 1% |
| Water | 49% |

This formulation can be used as a spray by diluting into water or applied directly to seed.

EXAMPLE 14

A wettable powder formulation is made by mixing together and grinding the ingredients until all are throughly mixed.

| Compound No. 1 of Table I | 25% |
| Sodium lauryl sulphate | 2% |
| Sodium lignosulphonate | 5% |
| Silica | 25% |
| China clay | 43% |

EXAMPLE 15

The compounds were tested against a variety of foliar fungal diseases of plants. The technique employed was as follows.

The plants were grown in John Innes Potting Compost (No. 1 or 2) in 4 cm diameter minipots. The test compounds were formulated by bead milling with aqueous DISPERSOL T which was diluted to the required concentration immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i. in dry soil. TWEEN 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:

4 = no disease

3 = trace —5% of disease on untreated plants

2 = 6-25% of disease on untreated plants

1 = 26-59% of disease on untreated plants

0 = 60-100% of disease on untreated plants

The results are shown in Tables III and IV.

CHEMICAL FORMULAE
(in description)

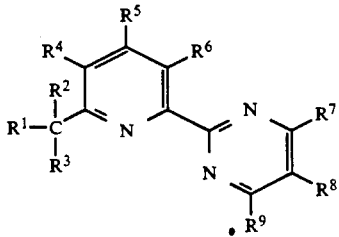 (I)

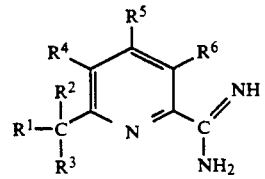 (II)

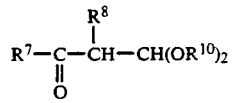 (III)

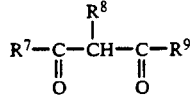 (IV)

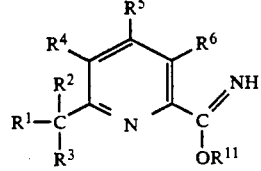 (V)

TABLE III

| Compound No | Puccinia recondita (Wheat) | Erysiphe graminis hordei (Barley) | Venturia inaequalis (Apple) | Pyricularia oryzae (Rice) | Thanetophorus cucumberis (Rice) | Septoria nodorum | Plasmopara viticola (Vine) | Phytophthora infestans (Tomato) |
|---|---|---|---|---|---|---|---|---|
| 1 | 0 | 2 | | | | 1 | 1 | |
| 2 | 4 | 4 | 4 | 4 | 0 | 4 | 0 | 2 |

TABLE IV

| Compound No | Puccinia recondita (Wheat) | Erysiphe graminis tritici (Wheat) | Venturia inaequalis (Apple) | Pyricularia oryzae (Rice) | Thanetophorus cucumberis (Rice) | Septoria nodorum | Plasmopara viticola (Vine) | Phytophthora infestans (Tomato) |
|---|---|---|---|---|---|---|---|---|
| 3 | 0 | 4 | 4 | 3 | | 4 | 0 | 4 |
| 5 | 4 | 4 | 4 | 4 | | 4 | 0 | 3 |
| 7 | | 4 | 4 | | 1 | 3 | 0 | 3 |
| 8 | 2 | 4 | 4 | 4 | 0 | 4 | 3 | 1 |
| 9 | 4 | 4 | 4 | 3 | 1 | 4 | 0 | 1 |
| 15 | 0 | 4 | 4 | 2 | 0 | 4 | 3_ | 0 |
| 19 | 0 | 0 | 4 | 4 | | 4 | 1 | 4 |
| 23 | 0 | 0 | 4 | 3 | | 0 | 0 | 4 |
| 30 | 4 | 4 | 4 | 4 | | 4 | 1 | 4 |
| 31 | 4 | 0 | 4 | | | | 0 | 3 |
| 32 | 4 | 0 | 4 | | | | 2 | 3 |
| 33 | 4 | 4 | 4 | 4 | 0 | 4 | 4 | 3 |
| 34 | 1 | 2 | 4 | 4 | 0 | 4 | 0 | 0 |
| 35 | 0 | 2 | 4 | 2 | 0 | 4 | 1 | 1 |
| 36 | 2 | 4 | 1 | 4 | 0 | 4 | 1 | |
| 37 | $0^a$ | $0^a$ | $4^a$ | $4^a$ | $0^a$ | $4^a$ | $2^a$ | $0^a$ |

$^a$25 ppm foliar application only.

-continued
CHEMICAL FORMULAE
(in description)

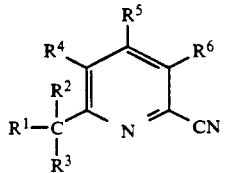 (VI)

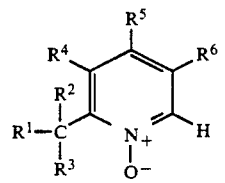 (VII)

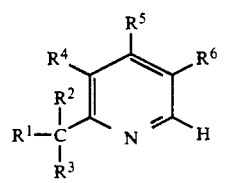 (VIII)

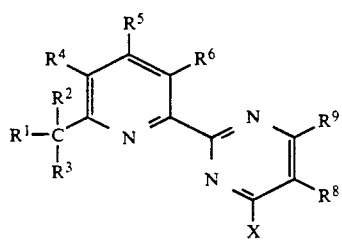 (IX)

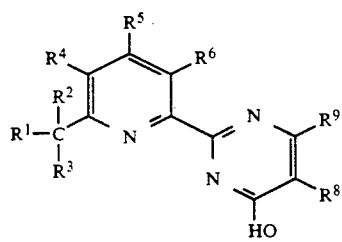 (X)

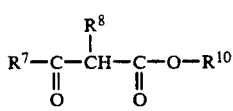 (XI)

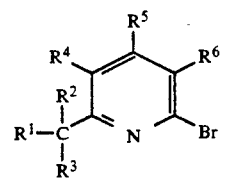 (XII)

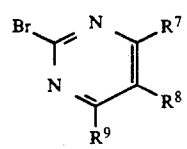 (XIII)

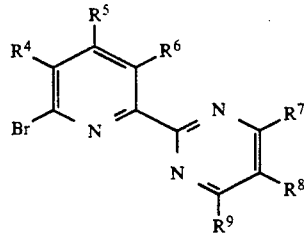 (XIV)

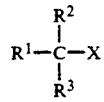 (XV)

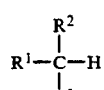 (XVI)

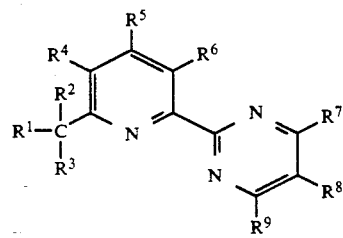 (XVII)

We claim:
1. A compound of general formula (I):

wherein $R^1$ is phenyl or phenyl group substituted with halogen, $C_{1-4}$ alkyl, $C_{1-4}$ alkoxy, $C_{1-4}$ haloalkoxy, $C_{2-4}$ alkenyl, $C_{2-4}$ alkynyl, $C_{1-4}$ haloalkyl, phenyl, benzyl, phenoxy or benzyloxy, wherein phenoxy, benzyl and benzyloxy are optionally substituted with halogen, $C_{1-4}$ alkyl, $C_{1-4}$ haloalkyl, $C_{1-4}$ alkoxy or $C_{1-4}$ haloalkoxy; $R^2$ and $R^3$, which are the same or different, are hydrogen or $C_{1-4}$ alkyl; $R^4$, $R^5$ and $R^6$, which are the same or different, are hydrogen, $C_{1-4}$ haloalkyl, $C_{1-4}$ alkyl or $C_{1-4}$ alkoxy; $R^7$, $R^8$ and $R^9$, which are same or different, are hydrogen, $C_{1-4}$ alkyl, $C_{1-4}$ haloalkyl, $C_{1-4}$ alkoxy or halogen, or $R^7$ and $R^8$ together form a polymethylene group of the formula —$(CH_2)_m$— in which m is 3 or 4; and, acid addition salts or metal complexes thereof.

2. A compound as claimed in claim 1 having the general formula (I), wherein $R^1$ is phenyl optionally substituted with halogen, $C_{1-4}$ alkyl, $C_{1-4}$ alkoxy, $C_{1-4}$ haloalkyl, $C_{2-4}$ haloalkoxy, $C_{2-4}$ alkenyl, $C_{1-4}$ alkynyl, phenyl, phenoxy, benzyl or benzyloxy wherein the phenyl, phenoxy, benzyl and benzyloxy moieties are optionally substituted with halogen, $C_{1-4}$ alkyl, $C_{1-4}$ haloalkyl, $C_{1-4}$ alkoxy or $C_{1-4}$ haloalkoxy; $R^2$ and $R^3$ are independently hydrogen or $C_{1-4}$ alkyl; $R^4$, $R^5$ and $R^6$ are independently hydrogen, $C_{1-4}$ alkyl, $C_{1-4}$ haloalkyl or $C_{1-4}$ alkoxy; $R^7$, $R^8$ and $R^9$ are independently hydrogen, halogen, $C_{1-4}$ alkyl, $C_{1-4}$ haloalkyl or $C_{1-4}$ alkoxy; and acid addition salts or metal complexes thereof.

3. A compound as claimed in claim 1 or 2 having the general formula (I), wherein $R^1$ is phenyl optionally substituted with halogen, $C_{1-4}$ alkyl especially methyl, $C_{1-4}$ alkoxy especially methoxy, $C_{1-4}$ haloalkyl especially trifluoromethyl or $C_{1-4}$ haloalkoxy especially trifluoromethoxy; $R^2$ and $R^3$ are independently hydrogen or $C_{1-4}$ alkyl especially methyl; $R^4$ is hydrogen, $C_{1-4}$ alkyl especially methyl or $C_{1-4}$ alkoxy especially methoxy, $R^5$, $R^6$, $R^8$ and $R^9$ are hydrogen; $R^7$ is hydrogen or $C_{1-4}$ alkyl especially methyl; and acid addition salts or metal complexes thereof.

4. A compound as claimed in claim 1, 2 or 3 having the general formula (I), wherein $R^1$ is phenyl optionally substituted with halogen, $C_{1-4}$ alkyl, $C_{1-4}$ alkoxy, $C_{1-4}$ haloalkyl or $C_{1-4}$ haloalkoxy; $R^2$ and $R^3$ are independently hydrogen or methyl; $R^4$, $R^5$, $R^6$, $R^8$ and $R^9$ are all hydrogen; $R^7$ is methyl; and acid addition salts or metal complexes thereof.

5. A compound as claimed in 1, 2, 3 or 4 having the general formula (I), wherein $R^1$ is phenyl optionally substituted with chlorine, fluorine, bromine, methyl, methoxy, trifluoromethyl or trifluoromethoxy; $R^2$ and $R^3$ are independently hydrogen or methyl; $R^4$, $R^5$, $R^6$, $R^8$ and $R^9$ are all hydrogen; $R^7$ is methyl; and acid addition salts or metal complexes thereof.

6. A fungicidal composition comprising a fungicidally effective amount of a compound according to claim 1 and a fungicidally acceptable carrier or diluent therefor.

7. A method of combating fungi which comprises applying to plants, to the seeds of plants or to the locus of the plants or seeds, a compound according to claim 1 or a composition according to claim 6.

* * * * *